(12) United States Patent
Kramer et al.

(10) Patent No.: US 9,448,201 B2
(45) Date of Patent: Sep. 20, 2016

(54) IN SITU PROBE WITH IMPROVED DIAGNOSTICS AND COMPENSATION

(71) Applicant: Rosemount Analytical, Inc., Solon, OH (US)

(72) Inventors: James D. Kramer, Homerville, OH (US); Joseph C. Nemer, Mayfield Heights, OH (US); Anni S. Wey, Strongsville, OH (US); Douglas E. Simmers, Massillon, OH (US); Mark Stojkov, Parma, OH (US)

(73) Assignee: Rosemount Analytical, Inc., Solon, OH (US)

( * ) Notice: Subject to any disclaimer, the term of this patent is extended or adjusted under 35 U.S.C. 154(b) by 233 days.

(21) Appl. No.: 14/224,680

(22) Filed: Mar. 25, 2014

(65) Prior Publication Data

US 2014/0290329 A1 Oct. 2, 2014

Related U.S. Application Data

(60) Provisional application No. 61/806,629, filed on Mar. 29, 2013.

(51) Int. Cl.
| | |
|---|---|
| *G01N 27/41* | (2006.01) |
| *G01N 27/417* | (2006.01) |
| *G01N 27/406* | (2006.01) |
| *F23N 5/00* | (2006.01) |

(52) U.S. Cl.
CPC ........... *G01N 27/4175* (2013.01); *F23N 5/006* (2013.01); *G01N 27/4065* (2013.01); *F23N 2027/20* (2013.01)

(58) Field of Classification Search
CPC ................... G01N 27/4065; G01N 27/4175; F23N 5/006
See application file for complete search history.

(56) References Cited

U.S. PATENT DOCUMENTS

| | | |
|---|---|---|
| 4,112,737 A | 9/1978 | Morgan |
| 5,010,776 A | 4/1991 | Lucero et al. |
| 6,846,458 B1 | 1/2005 | Staphanos |
| 6,862,915 B2 | 3/2005 | Staphanos et al. |
| 7,927,883 B2 | 4/2011 | Tuli et al. |
| 8,186,211 B2 | 5/2012 | Boult et al. |
| 8,342,019 B2 | 1/2013 | Hokamura |
| 2004/0182133 A1 | 9/2004 | Staphanos et al. |

(Continued)

OTHER PUBLICATIONS

First Office Action from Chniese Patent Application No. 201310364230.1 dated Nov. 20, 2015, 18 pages with English Translation.

(Continued)

*Primary Examiner* — Paul West
(74) *Attorney, Agent, or Firm* — Christopher R. Christenson; Kelly, Holt & Christenson, PLLC

(57) ABSTRACT

A process combustion transmitter is provided. The transmitter includes a process probe extendible into a flow of process combustion exhaust. The process probe has a measurement cell and a diffuser that define a chamber within the process probe. Electronic circuitry is coupled to the measurement cell and is configured to provide an indication relative to a combustion process based on an output signal of the measurement cell. A pressure sensor is coupled to the electronic circuitry and is fluidically coupled to the chamber. The electronic circuitry is configured to provide an adjusted calibration based on pressure measured within the chamber during a calibration.

16 Claims, 4 Drawing Sheets

(56) References Cited

U.S. PATENT DOCUMENTS

| | | | |
|---|---|---|---|
| 2009/0223820 A1* | 9/2009 | Ishiguro | G01N 27/419 204/424 |
| 2010/0300175 A1 | 12/2010 | Hokamura | |
| 2011/0012040 A1 | 1/2011 | Bailey | |
| 2012/0125840 A1 | 5/2012 | Smith | |
| 2014/0260511 A1 | 9/2014 | Nemer et al. | |

OTHER PUBLICATIONS

International Search Report and Written Opinion from International Application No. PCT/US2014/032016, date of mailing: Sep. 1, 2014, date of filing: Mar. 27, 2014. 11 pages.

International Search Report and Written Opinion from International Application No. PCT/US2014/023459, date of mailing: Jul. 17, 2014. 12 pages.

Product Data Sheet (DS 106-6888). "In Situ Flue Gas Oxygen Transmitter", by Rosemount Analytical, Emerson Process Management, Jan. 2012. 16 pages.

"Plugged Diffusion Element Diagnostic Feature", http://www.analyticexpert.com/2012/11/1557/, by Rosemount Analytical, Nov. 15, 2012, 1 page.

First Patent Examination Report for Australian Patent Application No. 2014241145, dated Jan. 21, 2016, 3 pages.

First Office Action for Chinese Patent Application No. 201480003735.8 dated Apr. 5, 2016, 12 pages.

* cited by examiner

IN SITU PROBE WITH IMPROVED DIAGNOSTICS AND COMPENSATION

CROSS-REFERENCE TO RELATED APPLICATION

The present application is based on and claims the benefit of U.S. Provisional Patent Application Ser. No. 61/806,629, filed Mar. 29, 2013, the content of which is hereby incorporated by reference in its entirety.

BACKGROUND

Industrial process industries primarily rely upon energy sources that include one or more combustion processes. Such combustion processes include operation of a furnace or boiler to generate energy from combustion, which is then used for the process. While combustion provides relatively low-cost energy, its use is typically regulated and combustion efficiency is sought to be maximized. Accordingly, one goal of the process management industry is to reduce the production of greenhouse gases by maximizing combustion efficiency of existing furnaces and boilers.

In situ or in-process analyzers are commonly used for the monitoring, optimization, and control of combustion processes. Typically, these analyzers employ sensors that are heated to relatively high temperatures and are operated directly above, or near, the furnace or boiler combustion zone. Combustion analyzers, such as those sold under the trade designation Oxymitter or Model 6888 Combustion Flue Gas Transmitter available from Rosemount Analytical, Inc. of Solon, Ohio (a business unit of Emerson Process Management), often employ zirconia oxide sensors heated to a temperature above approximately 700° Celsius (1300° Fahrenheit).

In situ analyzers generally employ a sintered metal filter or other diffuser positioned between a measurement cell and the process combustion gas to allow the process combustion gas to diffuse to the measurement zone while minimizing flow effects and reducing measurement cell contamination. The diffuser readily allows the process combustion gas to contact the heated measurement cell. However, if the diffuser should become partially or fully plugged, it can introduce errors into the measurement. Thus, providing an in situ oxygen probe that is better able to diagnose diffuser obstructions and/or compensate for effects of such obstructions would advance the art of process analytic measurement and control.

SUMMARY

A process combustion transmitter is provided. The transmitter includes a process probe extendible into a flow of process combustion exhaust. The process probe has a measurement cell and a diffuser that define a chamber within the process probe. Electronic circuitry is coupled to the measurement cell and is configured to provide an indication relative to a combustion process based on an output signal of the measurement cell. A pressure sensor is coupled to the electronic circuitry and is fluidically coupled to the chamber. The electronic circuitry is configured to provide an adjusted calibration based on pressure measured within the chamber during a calibration.

DETAILED DESCRIPTION OF ILLUSTRATIVE EMBODIMENTS

Figure 1:
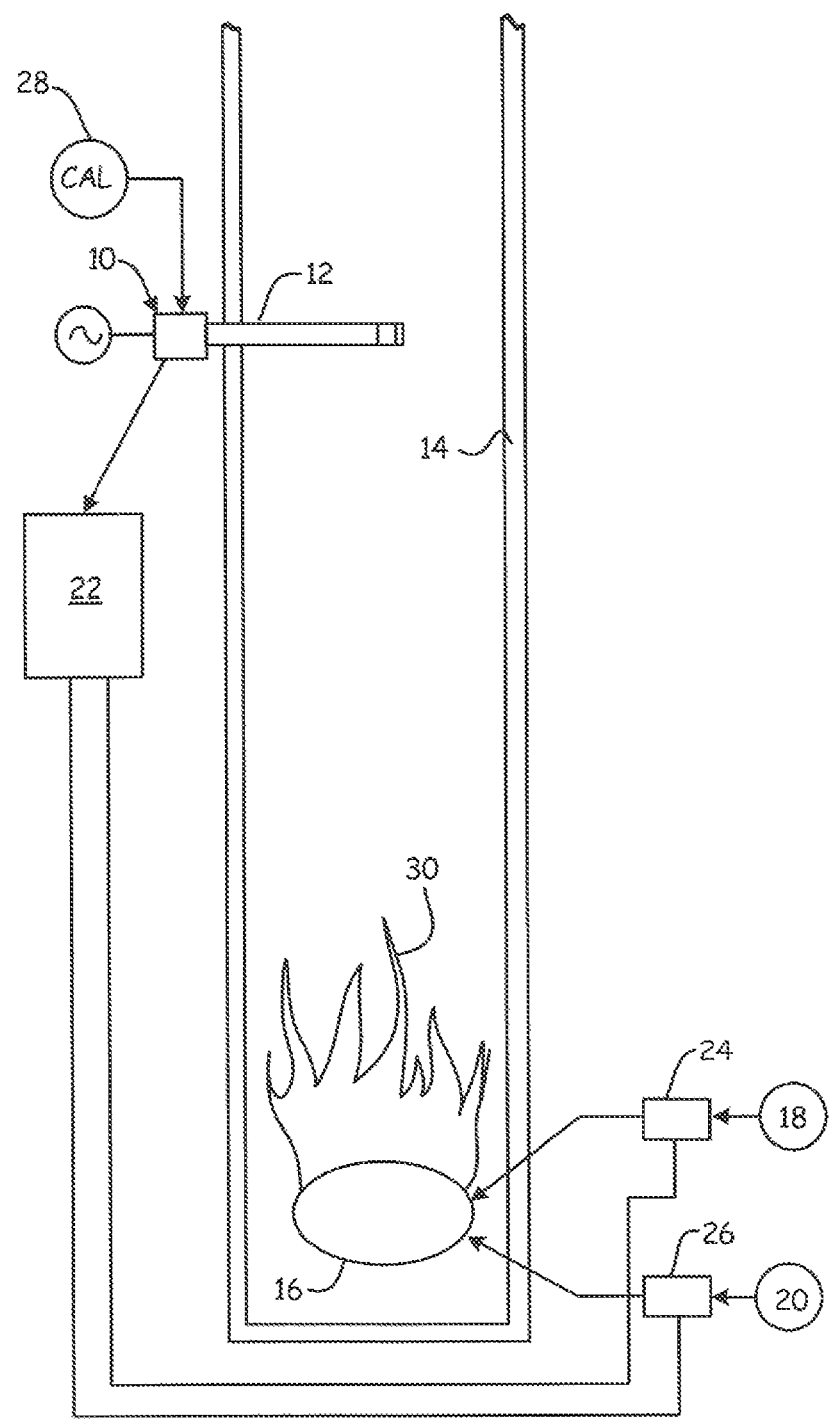
FIG. 1 is a diagrammatic view of an in situ analyzer with which embodiments of the present invention are particularly useful.

FIG. 1 is a diagrammatic view of an in situ process combustion analyzer. Transmitter 10 can be any suitable analyzer including the X-Stream $O_2$ Combustion Flue Gas Transmitter listed above. Transmitter 10 includes a probe assembly 12 that is disposed within a stack or flue 14 and measures at least one parameter related to combustion occurring at burner 16. Typically, transmitter 10 is an oxygen transmitter, but can be any device that measures any suitable parameter related to the combustion process. Burner 16 is operably coupled to a source of air or oxygen 18 and a source 20 of combustible fuel. Each of sources 18 and 20 is preferably coupled to burner through a valve of some sort to deliver a controlled amount of oxygen and/or fuel to burner 16 in order to control the combustion process. Transmitter 10 measures the amount of oxygen in the combustion exhaust flow and provides an indication of the oxygen level to combustion controller 22. Controller 22 controls one or both of valves 24, 26 to provide closed-loop combustion control. Transmitter 10 includes an oxygen sensor that typically employs a zirconia oxide sensor substrate to provide an electrical signal indicative of oxygen concentration, content or percentage in the exhaust.

Periodically and/or whenever otherwise desired, transmitter 10 is calibrated by providing a calibration gas from source 28 to probe 12. By measuring the response of the sensor(s) within probe 12 to the calibration gas, errors can be detected and compensated. In some instances, published specifications call for a minimum flow rate of the calibration gas in order to ensure that the cell area is entirely filled with calibration gas and that no flue gasses can mix with the calibration test gasses. In one specification, a minimum calibration gas flowrate of 5 SCFH is required.

Over a period of months or years, the diffuser element of probe 12 can become fully or partially plugged. When this occurs, the minimum flowrate required by some published specifications (such as 5 SCFH) will only be achieved at elevated pressures. In the case of manual calibration, a technician will increase calibration gas pressure until the desired flowrate is observed. For example, an instrument technician may perform a calibration with a badly plugged diffuser and notice when the bottle of calibration gas is opened that a 20 PSI calibration gas pressure only provides a 2 SCFH flow instead of the nominal 5 SCFH flow. In this instance, the technician will adjust the calibration gas pressure regulator until the desired 5 SFCH is achieved. The resulting pressure required to achieve such flow rate may be higher than 20 PSI, and may even pressurize the measurement cell of the probe assembly to some extent. Even a calibration performed where the measurement cell is pressurized on the order of 2 PSI (approximately 56 inches/ 1422.4 mm of water column) will affect the calibration process itself and introduce errors. This is because the measurement cell will return to normal operating pressures after calibration and will read an erroneous value, such as an artificially low (0.5% $O_2$) value. Moreover, when the diffuser is partially or completely plugged, calibration gas may be trapped between the measurement cell and the diffuser thus undesirably influencing the process variable measurements.

Additionally, during operation, when the diffuser becomes partially plugged, it causes the response time of the process variable to slow, due to slower diffusion of the combustion or exhaust gasses through the partially or completely plugged diffuser to the measurement cell.

In accordance with an aspect of the present invention, the backpressure of the calibration gas and/or the pressure proximate the measurement cell itself is measured during calibration. Since the measurement cell seals one side of the probe, the calibration gas must flow or otherwise diffuse out through the diffuser. Thus, if the diffuser is blocked, partially or completely, the calibration gas will not be able to escape and the backpressure or chamber pressure will rise. If the pressure is measured and exceeds a threshold, an indication of plugging can be provided. This indication can be provided by an alarm annunciated locally at the device, transmitted through a process communication loop or segment, or both. Further, the magnitude of the pressure observed during calibration can be related to a calibration error that can be compensated. Further still, additional remedial measures can also be taken based on the amount of plugging. For example, if the diffuser is 50% plugged, the transmitter may wait longer after calibration before providing process variable measurements in order to allow the calibration gas more time to escape through the partially plugged diffuser.

Figure 2:
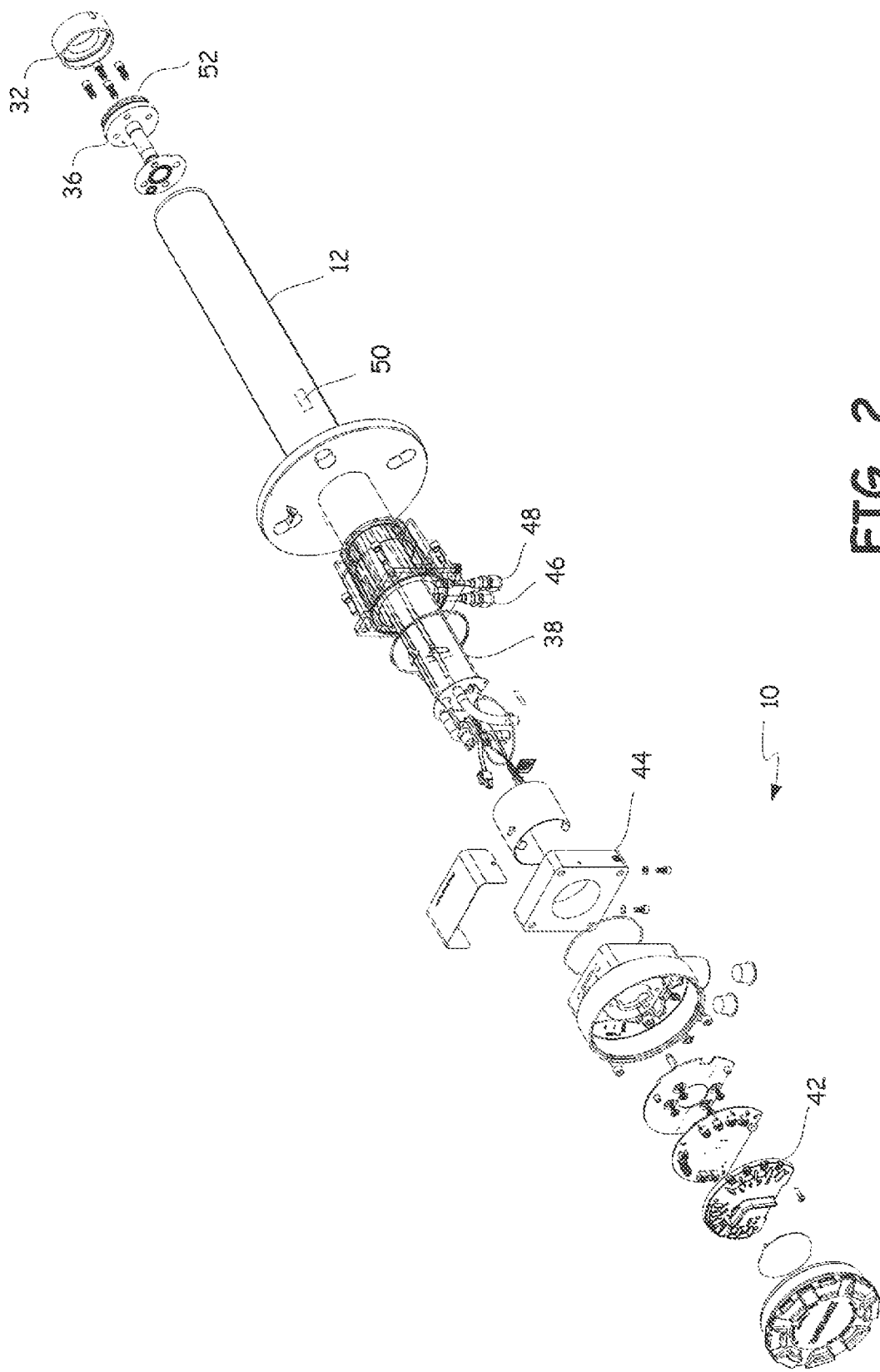
FIG. 2 is a diagrammatic exploded view of a process analytic oxygen transmitter in accordance with an embodiment of the present invention.

FIG. 2 is a diagrammatic view of an in situ process combustion analyzer in accordance with an embodiment of the present invention. Probe assembly 12 is generally configured to house a sensor core assembly which includes diffuser 32 disposed next to measurement cell 36. Measurement cell 36 and heater assembly 38 are electrically coupled to electronic circuitry contained on electronics board 42 in housing 44. Transmitter 10 also includes a plurality of gas inlets 46 and 48 to receive reference air and calibration gas, respectively.

As illustrated in FIG. 2, transmitter 10 includes a pressure sensor 50 that is fluidically coupled to chamber or region 52 between measurement cell 36 and diffuser 32. In the embodiment shown in FIG. 2, pressure sensor 50 is disposed along the calibration gas line (shown coupled to inlet 48) and thus measures the pressure of calibration gas proximate region 52. However, in other embodiments, pressure sensor 50 may be disposed within region 52. Pressure sensor 50 is electrically coupled to electronic circuitry on electronics board 42. Thus, pressure sensor 50 is able to provide an electrical indication of pressure within region 52 during calibration, normal operation, or both. Pressure sensor 50 may be any suitable type of pressure sensor including a deflectable diaphragm, capacitance-based pressure sensor, a deflectable diaphragm strain gauge, resistance-based pressure sensor, or any other suitable type of pressure sensor. However, the pressure sensor should be configured for exposure to the relatively low pressures and relatively high temperatures of operating in the flue-gas environments. Additionally, pressure sensor 50 may be disposed close to the flue-gas or in the electronics housing area (safe).

Zirconia oxide sensing technology has historically measured process oxygen by using ambient or instrument air as a reference (20.95% oxygen). Periodically, the sensor within measurement cell 38 may need to be calibrated where a precisely controlled amount of oxygen can be introduced to the sensor and exposed to measurement cell 36. Accordingly, ports 46 and 48 are coupled to conduits that direct the reference and calibration gases to measurement cell 36. The reference gas is provided to a side of the zirconia oxide substrate that is away from the process gas. During calibration, however, calibration gas is supplied to the side of the zirconia substrate that is opposed to the side exposed to reference gas. In this manner, each side is exposed to a gas. The calibration gas should flood region 52 and flow out diffuser 32. However, if the diffuser is even partially plugged, the ability of the calibration gas to flow out diffuser 32 is reduced. This will result in an increased calibration gas pressure, as set forth above. If the calibration gas has a higher pressure than nominal, this higher pressure will generate an increased oxygen reading by the sensor of oxygen in the calibration gas. If the sensor is calibrated at this higher pressure, then, when the pressure is reduced to the normal operating pressure, the calibrated sensor will read too low. However, by measuring the actual pressure in region 52 during the calibration, this effect can be measured and compensated. Additionally, the magnitude of the pressure itself can be used to provide a general indication of the degree of diffuser plugging. Finally, the degree of plugging determined from the pressure measurement can be used to increase the amount of time that the transmitter waits after calibration before providing process oxygen measurements. Thus, in a partially plugged diffuser, the calibration gas is given more time to diffuse out of region 52 before process oxygen measurements are provided.

Figure 3:
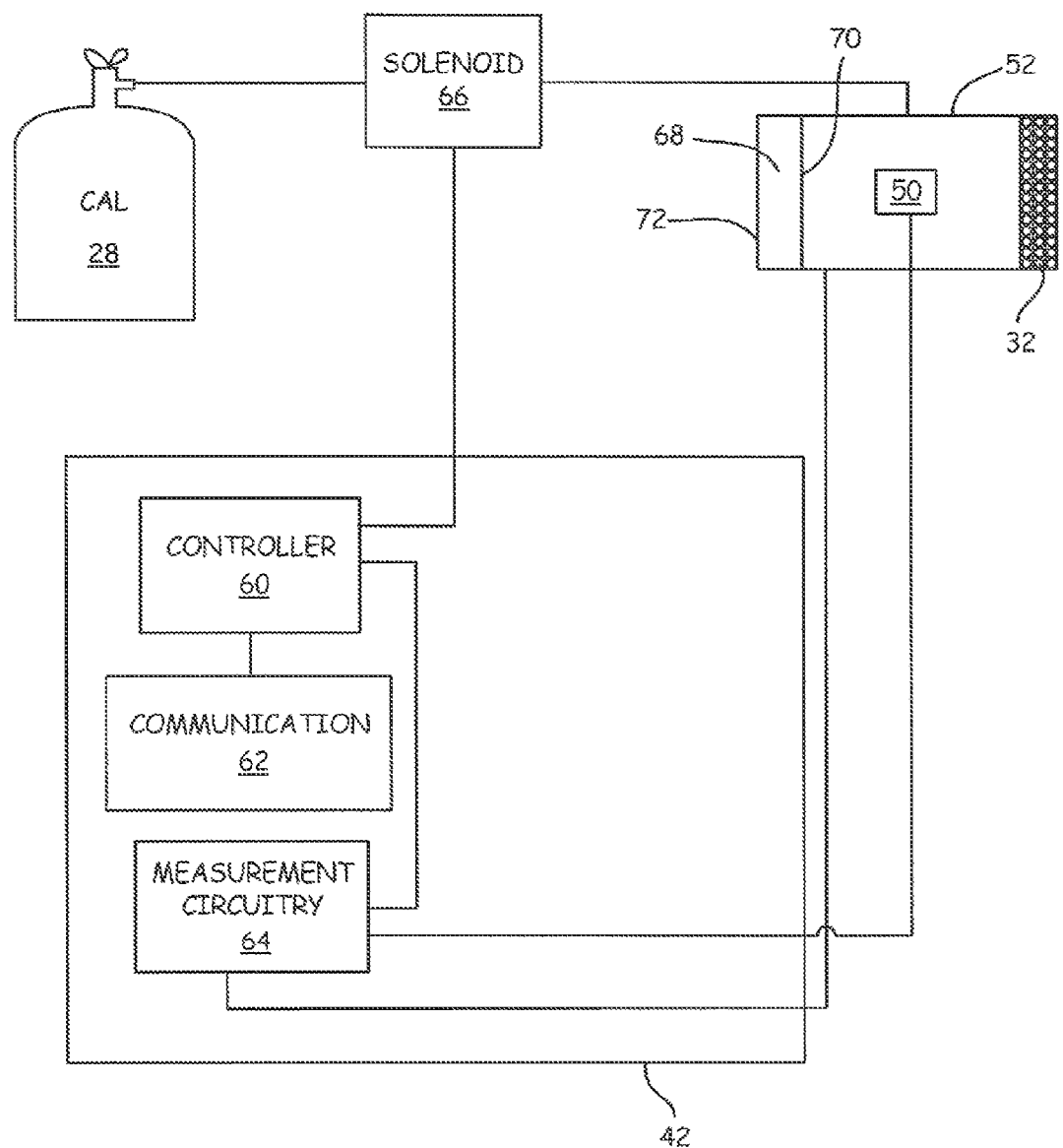
FIG. 3 is a block diagram of a process analytic oxygen transmitter in accordance with an embodiment of the present invention.

FIG. 3 is a block diagram of a process analytic oxygen transmitter in accordance with an embodiment of the present invention. For clarity, only a portion, region 52, of probe assembly 12 is depicted. However, FIG. 3 does indicate additional components of electronics board 42. Specifically, electronic circuitry on electronics board 42 includes controller 60 coupled to communication module 62 and measurement circuitry 64. Additionally, controller 60 is also operably coupled to solenoid 66, which controls the flow of calibration gas from source 28 to chamber 52. Controller 60 may be any suitable device that executes a sequence of instructions to perform one or more control functions. In one embodiment, controller 60 is a microprocessor.

Communication module 62 is coupled to controller 60 and allows controller 60 to communicate with one or more process devices, such as combustion controller 22 (shown in FIG. 1) in accordance with a wired process industry standard communication protocol. Examples of such protocols include the Highway Addressable Remote Transducer HART® Protocol and wireless process communication protocols, such as IEC 62591.

Measurement circuitry 64, in one embodiment, includes an analog-to-digital converter configured to measure an electrical characteristic, such as capacitance, of pressure sensor 50 that is indicative of pressure within chamber 52 and provide a digital indication of such to controller 60. Measurement circuitry 64 may also include suitable amplification, filtering, and/or linearizing circuitry as desired.

During normal operation, controller 60 maintains solenoid 66 in a disengaged state thus isolating calibration gas source 28 from chamber 52. Flue/combustion gasses from the combustion process diffuse through diffuser 32 and contact oxygen sensor 68. Oxygen sensor 68, in accordance with known techniques, will produce a voltage that is related to the difference in oxygen partial pressure between process side 70 in chamber 52 and reference side 72. This voltage is measured by suitable measurement circuitry, such as measurement circuitry 64 and indicated to controller 60. Controller 60 then communicates, via communication module 62, a process variable output to any suitable device, such as combustion controller 22.

Figure 4:
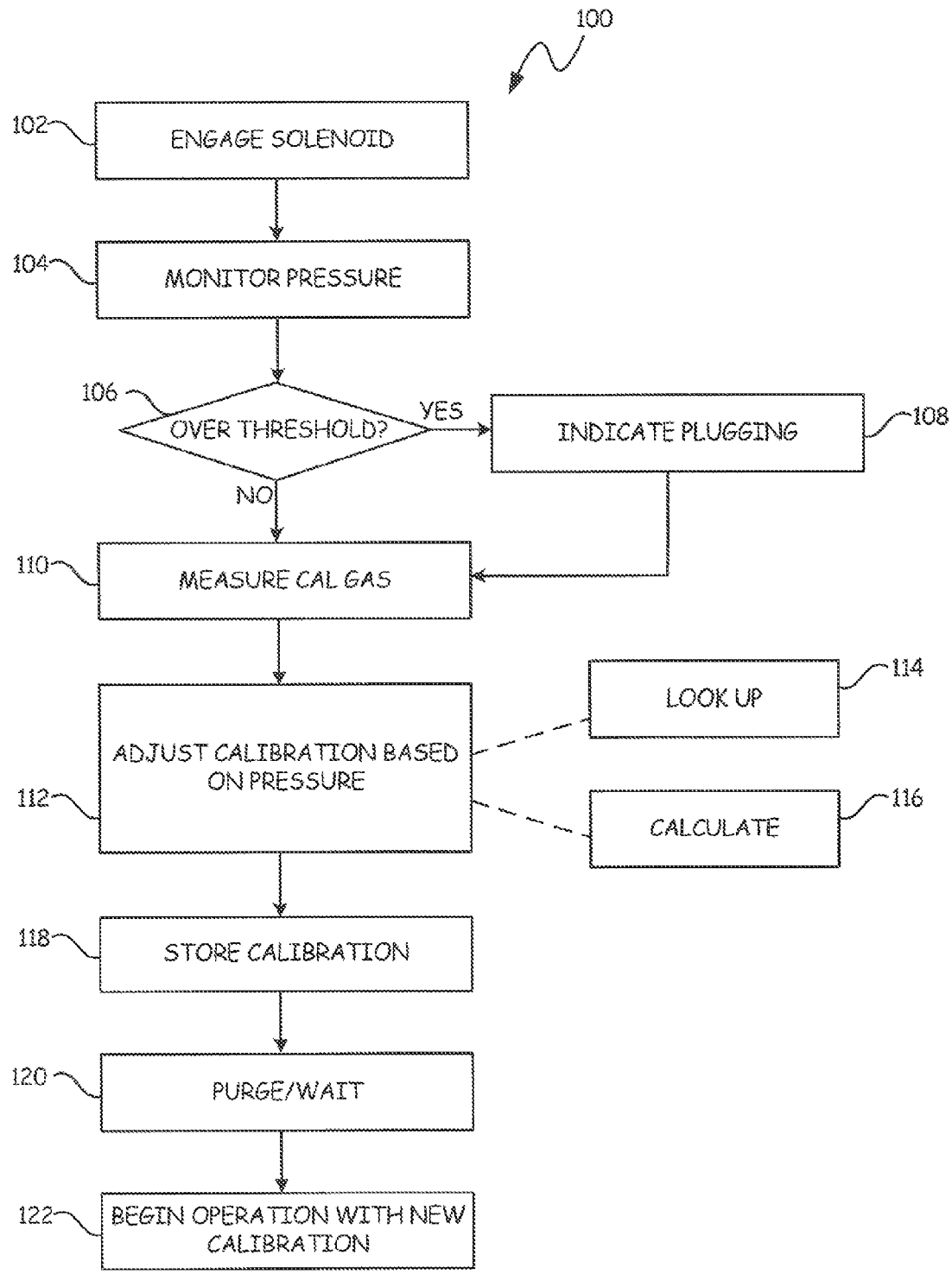
FIG. 4 is a flow diagram of a method of calibrating a process analytic oxygen transmitter in accordance with an embodiment of the present invention.

FIG. 4 is a flow diagram of a method of calibrating a process analytic oxygen transmitter in accordance with an embodiment of the present invention. The method indicated in FIG. 4, will also be described with respect to the block diagram of FIG. 3. Method 100 begins at block 102 where controller 60 engages solenoid 66 causing calibration gas from source 28 to flow into and fill chamber 52. Calibration gas will flow out of chamber 52 via diffuser 32. While the calibration gas is so flowing, controller 60 monitors the pressure within chamber 52 via pressure sensor 50 and measurement circuitry 64, as indicated at block 104. The monitored pressure is compared to a threshold at block 106, and if the pressure is above the threshold, then controller 60 will indicate diffuser plugging at block 108. This indication can be via a local annunciation, via communication through module 62, or both. Once the plugging annunciation/indication is generated, control passes to block 110. Additionally, if the monitored pressure is not above the threshold, then control passes simply from block 106 to block 110.

At block 110, the output of sensor 68 in response to the calibration gas is obtained. At block 112, the calibration is adjusted based on the pressure measured during block 104. Thus, if the diffuser is partially plugged and the pressure becomes high enough to generate calibration errors, such pressure can be measured and the calibration itself is adjusted based on the pressure. The relationship between the measured pressure and the effect on calibration can be characterized in any suitable format including a lookup table 114 or a curve-fit calculation, 116. These relationships can be obtained through testing and provided by the manufacturer of the device. Once the adjustment is obtained, the new calibration value(s) is/are stored at block 118. Once the calibration value(s) is/are stored, controller 60 de-energizes solenoid 66 and the flow of calibration gas is ceased. At block 120, controller 60 waits until sufficient time has elapsed before proceeding to block 122 and beginning operation with the new calibration value(s). This wait period, in accordance with one embodiment of the present invention, is adjusted based on the pressure measured during block 104. Thus, if a higher pressure is measured (indicative of partial plugging), then it will take longer for the calibration gas to diffuse out of chamber 52. Thus, controller 60 will wait longer before proceeding to block 122.

While aspects and embodiments described herein generally measure pressure of the calibration gas during calibration, aspects of the invention can also include continuously measuring pressure proximate the measurement cell during normal operation. Since pressure in the process causes error in the sensor output, this allows a real-time pressure compensated sensor output. Thus, variations in the pressure within the flue can be measured and compensated as well.

While some techniques can provide an indication of a plugged diffuser based on the speed with which the sensor responds to process changes, it is believed that embodiments of the present invention will provide a faster and more quantified diagnostic than such techniques.

Although the present invention has been described with reference to preferred embodiments, workers skilled in the art will recognize that changes may be made in form and detail without departing from the spirit and scope of the invention.

What is claimed is:

1. A process combustion transmitter comprising;
   a process probe extendible into a flow of process combustion exhaust, the process probe having a measurement cell and a diffuser, the measurement cell and the diffuser defining a chamber within the process probe;
   electronic circuitry coupled to the measurement cell and configured to provide an indication relative to a combustion process based on an output signal of the measurement cell;
   a pressure sensor operably coupled to the electronic circuitry and fluidically coupled to the chamber; and
   wherein the electronic circuitry is configured to provide an adjusted calibration based on pressure measured within the chamber during a calibration, and wherein the electronic circuitry is configured to provide an indication of diffuser plugging based on pressure measured during the calibration.

2. The process combustion transmitter of claim 1, wherein the indication is a local annunciation.

3. The process combustion transmitter of claim 1, wherein the indication is communicated in accordance with a process communication protocol.

4. The process combustion transmitter of claim 1, wherein the electronic circuitry is configured to resume process measurements after calibration using the adjusted calibration.

5. The process combustion transmitter of claim 4, wherein the electronic circuitry is configured to wait a selected amount of time after calibration before resuming process measurements.

6. The process combustion transmitter of claim 5, wherein the amount of time is selected based on the pressure measured during calibration.

7. The process combustion transmitter of claim 1, wherein the electronic circuitry includes a controller coupled to measurement circuitry and wherein the measurement circuitry is operably coupled to the pressure sensor.

8. The process combustion transmitter of claim 7, and wherein the electronic circuitry further comprises a communication module coupled to the controller and configured to communicate in accordance with a process communication protocol.

9. A method of calibrating a process combustion transmitter, the method comprising:
   providing a flow of calibration gas into a chamber defined, at least partially, by a measurement cell and a diffuser;
   measuring a pressure of calibration gas in the chamber while the calibration gas is flowing;
   measuring the measurement cell response to the calibration gas;
   providing an adjusted calibration based on the measurement cell response and the measured pressure;
   providing an indication of diffuser plugging based on the measured pressure.

10. The method of claim 9, wherein the measurement cell includes an oxygen sensor.

11. The method of claim 10, wherein the measurement cell is a zirconia oxide-based oxygen sensor.

12. The method of claim 9, and further comprising waiting a selected amount of time after the calibration to begin providing process measurements using the adjusted calibration.

13. The method of claim 12, wherein the selected amount of time is based on the pressure measured during calibration.

14. A method of calibrating a process combustion transmitter, the method comprising:

providing a flow of calibration gas into a chamber defined, at least partially, by a measurement cell and a diffuser;

measuring a pressure of calibration gas in the chamber while the calibration gas is flowing;

measuring the measurement cell response to the calibration gas;

providing an adjusted calibration based on the measurement cell response and the measured pressure; and measuring a pressure within the chamber during normal operation and providing a compensated process variable output.

15. The method of claim 14, and further comprising waiting a selected amount of time after the calibration to begin providing process measurements using the adjusted calibration.

16. The method of claim 15, wherein the selected amount of time is based on the pressure measured during calibration.

* * * * *